United States Patent
Blatter et al.

(10) Patent No.: US 7,504,071 B2
(45) Date of Patent: Mar. 17, 2009

(54) SEALING SYSTEM WITH FLOW CHANNELS

(75) Inventors: Fritz Blatter, Reinach (CH); Brigitte Cron-Eckhardt, Binningen (CH); Urs Christoph Hofmeier, St. Pantaleon (CH); Peter Koller, Lausen (CH); Claudia Marcolli, Zürich (CH); Martin Szelagiewicz, Münchenstein (CH)

(73) Assignee: Solvias AG, Basel (CH)

( * ) Notice: Subject to any disclaimer, the term of this patent is extended or adjusted under 35 U.S.C. 154(b) by 966 days.

(21) Appl. No.: 10/489,104

(22) PCT Filed: Sep. 13, 2002

(86) PCT No.: PCT/EP02/10280

§ 371 (c)(1),
(2), (4) Date: Mar. 10, 2004

(87) PCT Pub. No.: WO03/026797

PCT Pub. Date: Apr. 3, 2003

(65) Prior Publication Data

US 2004/0239044 A1 Dec. 2, 2004

(30) Foreign Application Priority Data

Sep. 21, 2001 (CH) ............................. 2001 1747/01

(51) Int. Cl.
*B01L 11/00* (2006.01)
*B01L 3/00* (2006.01)
*B01L 9/00* (2006.01)
*B01J 10/00* (2006.01)

(52) U.S. Cl. .................... 422/101; 422/102; 422/103; 422/104; 422/129; 422/130

(58) Field of Classification Search ................ 422/102, 422/103, 104, 129, 130, 101
See application file for complete search history.

(56) References Cited

U.S. PATENT DOCUMENTS

| | | | |
|---|---|---|---|
| 4,673,651 A | 6/1987 | Rothenberg et al. | |
| 5,817,510 A | 10/1998 | Swami et al. | |
| 6,136,274 A * | 10/2000 | Nova et al. | ................. 506/33 |
| 6,239,875 B1 * | 5/2001 | Verheijen | ................. 356/436 |
| 6,277,642 B1 | 8/2001 | Danigel et al. | |

FOREIGN PATENT DOCUMENTS

| | | |
|---|---|---|
| DE | 89 04 501 | 11/1989 |
| DE | 89 12 115 | 11/1989 |
| DE | 295 19 602 | 4/1996 |
| EP | 0 400 965 | 12/1990 |
| WO | 02 24861 | 3/2002 |
| WO | 02 072423 | 9/2002 |
| WO | WO 02/072423 * | 9/2002 |

* cited by examiner

Primary Examiner—Walter D Griffin
Assistant Examiner—Lessanework Seifu
(74) Attorney, Agent, or Firm—Wenderoth, Lind & Ponack, L.L.P.

(57) ABSTRACT

A device includes a support (1) and at least two seals (2), which are arranged in a row and are hermetically fitted into cavities, and protrude from the support laterally with respect to inlet and outlet openings, one end of the support being provided with an inlet opening (3) and one end being provided with an outlet opening (4), and the seals being provided with a least one inlet opening and one outlet opening, and the support containing at least one first channel (5) which starts at the inlet opening (3) and is continuous, and is arranged in such a way that it opens into the inlet openings in the side walls of the seals arranged in a row, and one second channel (6) which starts at the outlet opening and is continuous, and is arranged in such a way that it opens into the outlet openings in the side walls of the seals arranged in a row. The system is suitable for simultaneous multiple studies, in particular with the use of microtitration plates, and physical measurements of the results directly in the containers, for example of a microtitration plate. The multiple studies may be used to perform screening processes to discover and develop polymorphic and pseudorpolymorphic forms, new formulations and suitable crystallisation conditions.

29 Claims, 2 Drawing Sheets

SEALING SYSTEM WITH FLOW CHANNELS

The present invention relates to a sealing system consisting of (a) a support and (b) at least two seals, which are arranged in a row and are hermetically fitted into cavities, and protrude from the support laterally with respect to inlet and outlet openings, one end of the support being provided with an inlet opening and one end being provided with an outlet opening, and the seals being provided with a least one inlet opening and one outlet opening, and the support containing at least one first channel which starts at the inlet opening and is continuous, and is arranged in such a way that it opens into the inlet openings in the side walls of the seals arranged in a row, and one second channel which starts at the outlet opening and is continuous, and is arranged in such a way that it opens into the outlet openings in the side walls of the seals arranged in a row: The sealing system is suitable for simultaneous multiple studies, in particular with the use of microtitration plates, and physical measurements of the results directly in the containers, for example of a microtitration plate.

The study of chemical reactions or physical properties of chemical substances under different conditions or the effect of different reactants is time-consuming and requires rather high amounts of substance, since multiple studies need to be carried out. Efforts have therefore been made for a long time to reduce the time taken and the amount of material needed, by using miniaturised systems such as microtitration plates, and methods have been developed in order to measure the characterisation of changes directly in the reaction vessel, for example by means of microscopic, spectroscopic, or diffractional methods.

There is, for example, interest in devices with which solvents can be evaporated and mixtures to be studied can be concentrated to dryness. The Zymark Corporation (Hopkinton, Mass., USA) has, to that end, provided a machine for concentrating solutions, in which two blocks, provided with cannulas arranged in wells, are fitted in a lid which can be opened, the number of which corresponds to the containers in a titration plate, so that inert gases can be sent through the wells of a titration plate. The company Barkey (Germany) provides a similar system, in which exposed steel cannulas can be used for conducting air.

These machines simultaneously address all the containers in a titration plate, which is not always required. Furthermore, measurements cannot be carried out directly in the vessels of the titration plate, or can be carried out only with great difficulty.

WO 00/67872 describes an automated system for studying polymorphic crystal forms, in which samples are taken from a storage container, filtered and then transferred into vessels of a titration plate by using a needle pipette, with different solvents being added to individual samples. It is also proposed, after evaporation of solvents, to carry out measurements directly in the containers of the titration plate, for example microscopy or Raman spectroscopy.

There is a need for a device which is easier to handle and can be used more flexibly, with which the number of vessels to be used can be selected, and different experiments can be carried out simultaneously under variable experimental conditions, with the possibility of feeding one or more gases through the vessels and processing at standard, elevated or reduced pressure. Furthermore, it is extremely desirable to be able to monitor newly formed materials resulting from changes directly in the reaction vessel, for example by means of microscopic, spectroscopic, or diffractional methods (X-ray diffraction including employment of synchrotron radiation).

BRIEF DESCRIPTION OF THE DRAWINGS

FIG. 1 shows the device with the support (1), the inlet opening (3), the outlet opening (4), eight seals (2) which are arranged in a row and are hermetically fitted in the support, and which have circumferential sealing lips (9) protruding from the support, the openings (10) and (11) in the seals (2), as well as glands (7) and (8) for connection to the inlet opening and outlet opening.

FIG. 2 shows a cross section in the longitudinal direction of the device according to FIG. 1 at the level with the channels, in order to represent the profile of the channels (5) and (6) from the inlet opening (3) and outlet opening (4).

FIG. 3 shows the other side of the device in FIG. 1, with the seals (2) flush with the surface of the support (1).

FIG. 4 shows a system according to the invention, consisting of a microtitration plate, in which eight wells are respectively connected hermetically to eight seals of two successively arranged devices according to FIG. 1 (or of one device with two rows).

Figure 1:
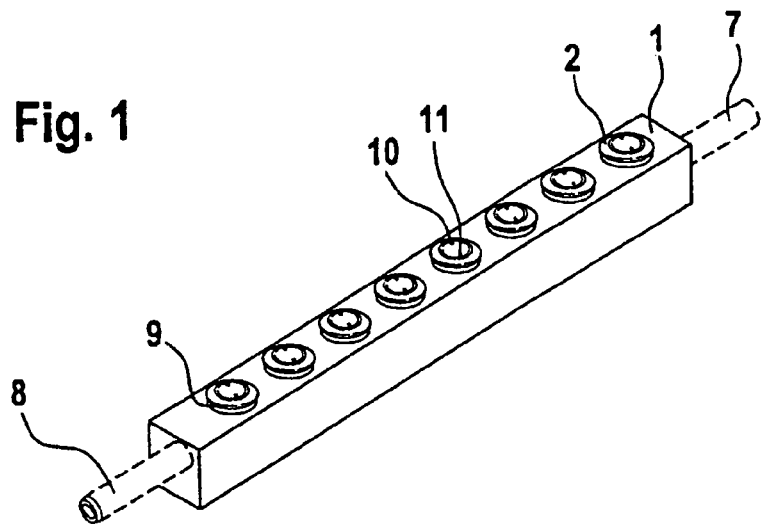
FIGS. 1, 1a, 2, 3 and 4 illustrate the device according to the invention and the system according to the invention.
Figure 1A:
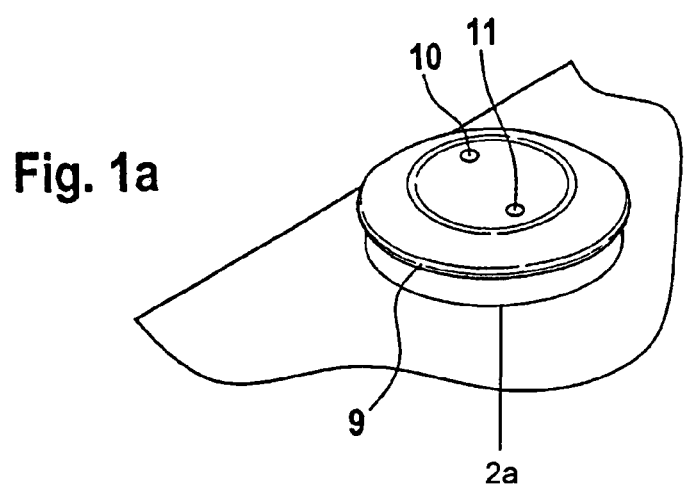
Figure 2:
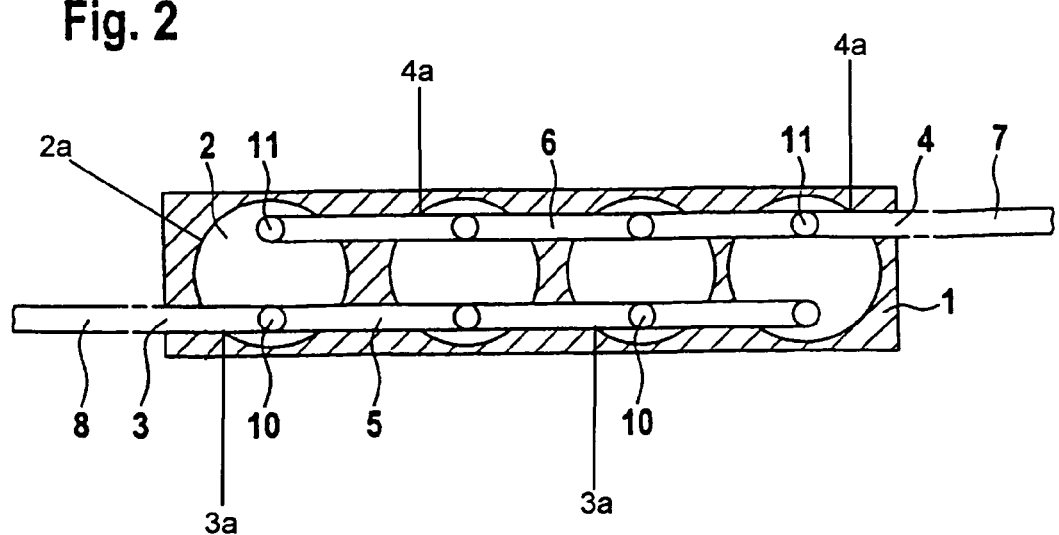
Figure 3:
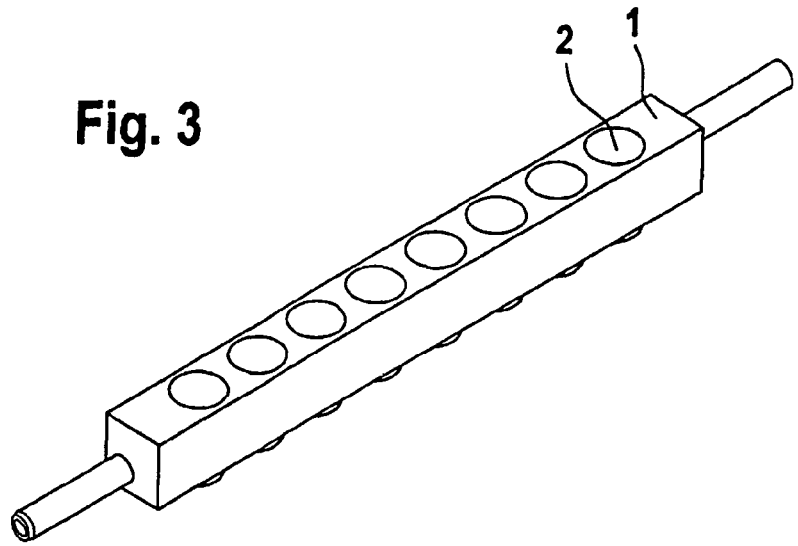
Figure 4:
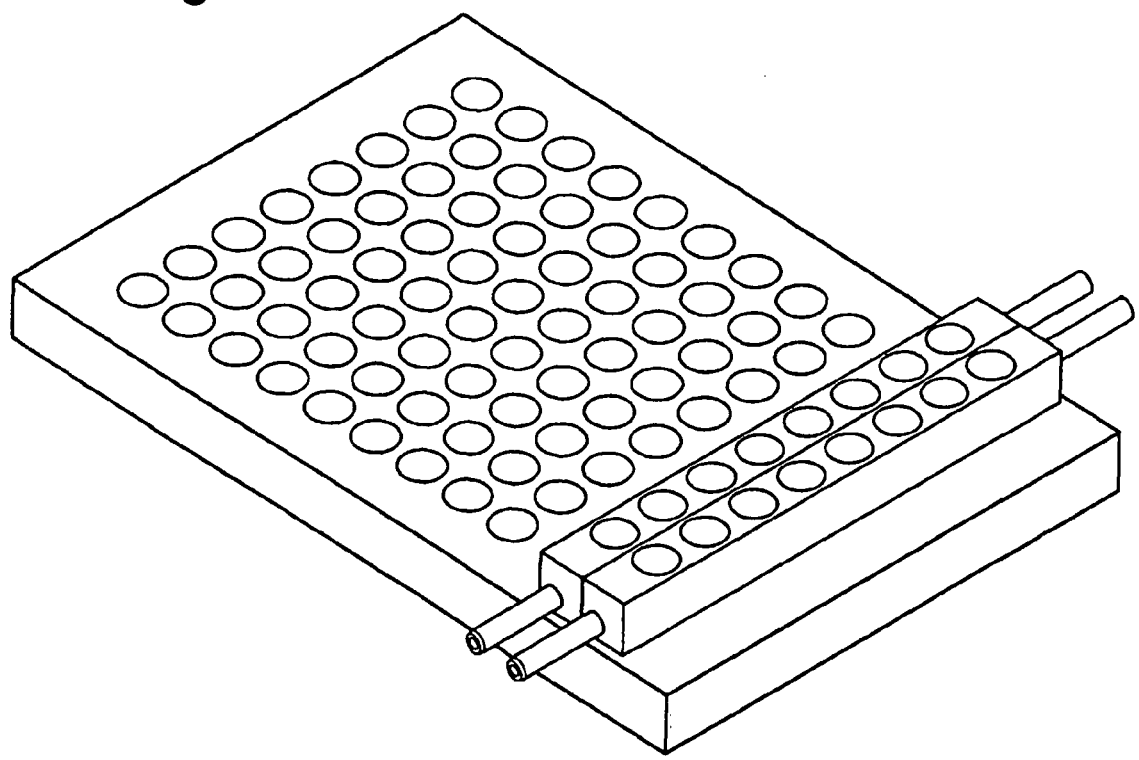

The invention firstly relates to a device consisting of a support (1) and at least two The invention first relates to a device consisting of a support (1) and at least two seals (2), which are arranged in a row and are hermetically fitted into cavities (2a), and protrude from the support laterally with respect to inlet and outlet openings, one end of the support being provided with an inlet opening (3) and one end being provided with an outlet opening (4), and the seals being provided with a least one inlet opening (10) and one outlet opening (11), and the support containing at least one first channel (5) which starts at the inlet opening (3) and is continuous, and is arranged in such a way that it opens into side inlet openings (3a) in the side walls of the seals arranged in a row, and one second channel (6) which starts at the outlet opening (4) and is continuous, and is arranged in such a way that it opens into side outlet openings (4a) in the side walls of the seals arranged in a row.

The inlet openings (3) and the outlet openings (4) may be arranged at one end or at opposite ends of the support. The inlet channel ends in the last seal and the outlet channel ends in the first seal through the connection to the inlet and outlet openings. The inlet and outlet channels may be designed in the last and first seals like the inlet and outlet openings, so that a continuous channel is provided, the ends of which can be closed or kept open during operation, mixing of gases being prevented by differing pressure. This embodiment can be used very flexibly.

The support may consist of a wide variety of materials, for example metals such as aluminum or stainless steel, glass, quartz, ceramic and optionally reinforced and stiff plastics. The plastics may be thermoplastics or thermosetting plastics. The size of the support will be selected in such a way that it contains at least two cavities. Advantageously, the support contains from 2 to 1000, preferably from 2 to 500, particularly preferably from 4 to 100 and more particularly preferably from 4 to 24 cavities lying in a row. The support may also be designed two-dimensionally, and contain two or more than two cavities lying in a row, for example from 2 to 1000, preferably from 2 to 500 and particularly preferably from 4 to 100 rows. In this configuration, the support constitutes a block which contains successively organised rows of cavities.

In an advantageous configuration, the support is designed in such a way that it corresponds to the length of the side of a macro- or microtitration plate, and to the containers arranged in a row thereof, and has cavities corresponding to the number of containers in a row of such a titration plate (one-dimensional arrangement). In another configuration, the support corresponds to the length of the side of a macro- or microtitration plate, and to the containers arranged in a row thereof, is designed two-dimensionally and has cavities which correspond to from at least two (for example from 2 to 4) to all the rows of containers in a titration plate are hermetically connected to a single-rowed arrangement of seals. In this configuration, the support constitutes a block which contains successively organised rows of cavities corresponding to the dimensions of a titration plate.

The support may have a thickness of from 2 mm to 8 cm, preferably from 4 mm to 4 cm, and particularly preferably from 6 mm to 3 cm.

The support contains at least two continuous cavities perpendicular to its longitudinal direction, which correspond essentially to the size of the seals to be accommodated. The geometrical shape per se is arbitrary, although cylindrical shapes which are open on both sides are preferred. The diameter of the cavities is preferably equal, and it and may, for example, be from 2 mm to 5 cm, preferably from 3 mm to 3 cm.

The support contains at least two channels, which are arranged essentially perpendicular to the cavities and connect the cavities. At least one of the channels is used as an inlet channel, and is configured in such a way that it opens from a first inlet outer port in the first cavity, connects all the other cavities and then opens in the last cavity. One channel is used as an outlet channel, and is configured in such a way that it opens from a second outer inlet port, lying at the other end opposite the first, in the last cavity, connects all the other cavities and then opens in the first cavity. The support may contain further inlet channels arranged equally and essentially parallel, for example in total from 2 to 4. The further inlet channels may end in the first cavity or connect together at least two or all the cavities. The support contains only one outlet channel.

The diameter of the channels may be selected according to the size of the cavities and desired flow rates of gases. The diameter may be in the micro range to the millimeter range, and for example from 10 pm to 10 mm, preferably from 50 pm to 5 mm and particularly preferably from 100 pm to 3 mm.

The support material preferably consists of metal, for example aluminum or stainless steel.

The mutually opposite openings of the inlet channels and of the outlet channel at the ends of the support may be provided with hermetically fitted glands, for example in the form of short tubes, which may be connected to gas sources (inlet channels) and/or optionally a vacuum pump. Depending on the material, these tubes may be soldered on, pressed into the channel, adhesively bonded or screwed in. They may also be designed as an extension of the support.

The production of the described support may be carried out using methods which are known per se, the choice of methods depending essentially on the material which is used. When using metals and other inorganic materials such as glass or quartz, the cavities and channels may be made by milling and boring. It is, however, possible to cast semifinished article with the cavities, in which the channels are formed by boring. When using plastics, the production of the support may take place likewise. It is, however, also possible to use plastics processing techniques to produce the support with cavities and channels in a single operation, for example casting or injection moulding methods, and subsequent curing if thermosetting plastics are being used. Milling and casting techniques may also be used to produce glands for the openings of the channels, which are then bored through.

If the diameters of the openings in the support are not too great, and the support is not too thick, ablative methods, for example laser lithography, or etching techniques may also be employed to produce the support, specifically to introduce the openings and channels in one operation or to form only the channels in a support, which already contains openings. The support then constitutes a composite made of two parts. The channels are in this case formed on the surface of a first plate which contains the openings, and are then hermetically covered, for example by adhesive bonding, with a second plate of equal size, made of the same material.

Hermetically closing seals are fitted into the openings of the support, and they are provided with bores which connect the inlet channels and the outlet channel of the support. The seals protrude from the lower side of the support, and optionally also from its upper side. Preferably, the seals terminate on the upper side flush with the surface of the support. The extent to which the seals protrude depends essentially on the shape of the vessels which are to be connected to the seals. The distance from the surface of a reaction mixture in the vessel is expediently selected in such a way that no substances escape. The seals may, for example, protrude by from 0.5 mm to 1 cm, depending on the depth of the vessel. The bores may have the same diameter as the channels in the support, or a smaller diameter. The seals may be provided with a thread and screwed into the openings of the support. They may also be adhesively bonded or pressed in, so as to create a hermetic closure which makes it possible to operate at standard, elevated or reduced pressure. If the seals are pressed in, a seal diameter which is slightly greater than the diameter of the openings in the support is expediently selected, in order to guarantee the desired leaktightness. A slightly conical profile towards the end of the protruding part makes it easier to insert the seal into vessels.

The seals advantageously have a flat surface at the protruding end. Above the surface, a circumferential sealing lip is preferably fitted, which permits a high application pressure and the desired leaktightness during connection to a vessel. Alternatively, it is also possible to provide a circumferential groove, into which a sealing ring is placed for this purpose. A further option is to provide another circumferential seal, which ensures tight closure during connection to vessels, at the junction of the support with the fitted seal.

The sealing material may, for example, consist of metal, in which case a screw connection to the support is advantageous. More expediently, the sealing material consists of a resilient material, for example thermoplastic or elastomeric plastics. The seals may also be readily produced from plastics by means of injection moulding or milling. Fluorinated hydrocarbons, for example poly-di- or poly-tetrafluoroethylene, which are inert with respect to many chemicals and guarantee a long working life, are particularly preferred plastics.

The openings of the inlet bores and the openings of the outlet bore at the end of the protruding part of the seal are advantageously arranged in such a way as to prevent escape of substances. Expediently, openings of the inlet bores and the openings of the outlet bore are fitted opposite on the edge of the seal. The openings of the inlet bores and the openings of the outlet bore on the sealing wall, which respectively open into the inlet and outlet channels of the support, are arranged at the level with the channel openings. These openings in the seals are preferably situated approximately in the mid-part of the part of the seal flush with the support. The arrangement of the bores in the seal may vary. If the intention is to make only one continuous bore, the bore extends from the mid-part of the seal obliquely to the lower end. It is, however, also possible to fit two bores, namely essentially horizontal and vertical to one another, in which case the vertical bore will in turn need to be hermetically closed at the other end from the inlet and outlet openings. A continuous bore is therefore preferred.

In one embodiment, the device may be configured in such a way that each seal in the support is additionally provided with a further individual inlet channel, which opens in a further inlet opening of the seal and connects this inlet opening to the other inlet opening of the seal via a channel. The openings of the individual inlet channels may be provided with hermetically fitted glands, for example in the form of short tubes. This embodied is primarily intended for the serial studies, in which different gases, gas mixtures or different quantities of gases or gas mixtures are to be introduced into vessels. To that end, the device may also be configured in such a way that the continuous inlet channel is omitted, that is to say replaced by the individual inlet channels.

The device according to the invention is outstandingly suitable for hermetic connection to at least two vessels in order to carry out a multitude of simultaneous studies of various types.

The invention furthermore relates therefore to a system consisting of (a) a device according to the invention and (b) at least 2 vessels which are hermetically connected to the seals.

The size of the vessels will advantageously be dimensioned in such a way that studies in the nanogram to microgram to gram quantity range can be carried out, for example in the range of from 1 pg to 10 g, preferably from 10 pg to 5 g and particularly preferably from 100 pg to 1 g. The size of the vessel will, in particular, preferably be selected in accordance with the study of micro-quantities, for example from 100 pg to 100 mg. It is furthermore expedient to provide a sufficient empty volume over the filled vessel, in order to avoid an undesired transfer of substances into other reaction spaces.

The vessels may be provided as individual vessels, or vessels connected in a one-dimensional or two-dimensional row arrangement, in which case at least two vessels are connected and at least two one-dimensional row arrangements may be aligned successively. These arrangements may be held together by clamps or in a frame, so as to guarantee the necessary stability for the studies and so that the arrangement can be shaken in order to homogenise reaction mixtures. The vessels may be made of a wide variety of materials, for example from metals, metal oxides, ceramic, glass or quartz. The choice of the materials depends on the chemicals used in the intended studies and on the measurement methods, with which chemical modifications or changes of a physical state are to be determined.

Preferably, the vessels involve a plate with wells at an equal spacing, in a one- or two-dimensional row arrangement, and preferably cylindrical wells with a flat or rounded bottom. The volume of the wells is advantageously from 10 pl to 5 ml and particularly preferably from 100 pl to 3 ml. The diameter of the wells may, for example, be from 10 pm to 3 cm and particularly preferably from 100 pm to 2 cm. Such plates are known and are commercially available as standardised macro- or microtitration plates with a defined number of wells. The 8×12 format with 96 wells, as well as the 4×6 format with 24 wells, the 6×8 format with 48 wells, the 16×24 format with 384 wells, are particularly widespread. The geometry of titration plates can be different, which can be selected for example from circular or angular shapes (square, rectangle).

The plates may consist of various materials, optically transparent materials being preferred since changes after a reaction or conversion of substances can be measured directly in the vessels by means of spectroscopic methods. Examples of suitable transparent materials include organic glasses, which may involve thermoplastic or thermosetting plastics, for example polymethacrylates, polycarbonate or polyester. Inorganic glasses are particularly suitable, of which quartz is the most particularly preferred. Further preferred materials are materials which are transparent to X-ray radiation or exhibit only weak interactions with X-rays.

In a preferred embodiment, the system according to the invention
Involvesn a In a preferred embodiment, the system according to the invention involves (a) a device consisting of a support with from 2 to 24, preferably from 4 to 16 seals (2), which are arranged in a row and are hermetically fitted into cavities (2a), and protrude from the support laterally with respect to inlet and outlet openings, one end of the support being provided with an inlet opening (3) and one end being provided with an outlet opening (4), and the seals being provided with a least one inlet opening (10) and one outlet opening (11), and the support containing at least one first channel (5) which starts at the inlet opening (3) and is continuous, and is arranged in such a way that it opens into the side inlet openings (3a) in the side walls of the seals arranged in a row, and one second channel (6) which starts at the outlet opening (4) and is continuous, and is arranged in such a way that it opens into the side outlet openings (4a) in the side walls of the seals arranged in a row; and (b) a titration plate made of an optically transparent material, to whose wells the seals of the device are hermetically connected.

The titration plate preferably consists of glass. In an advantageous configuration, the device consists of from 1 to 3 rows of seals arranged in a support, which correspond to the geometry of the titration plate with wells. The device with from 1 to 3 rows of seals may be connected individually to from one to three rows of wells, and it is possible to connect a plurality to them, successively or with the omission of individual or multiple rows of wells. Such arrangements provide the advantage that it is simultaneously possible to take measurements and prepare or carry out new conversions.

Particularly preferably, the device consists of a one-rowed arrangement of seals, which are hermetically connected to a corresponding wells of a titration plate. This system according to the invention can be used particularly flexibly, since conversions, measurements or preparations for conversions can be carried out in individual, multiple or all rows of wells of the titration plate. The substances do not need to be removed for the measurement of changes, for example in the near IR (NIR) or visible range. The radiation source may be directed onto the wells in the titration plate from the upper side or through the bottom of the titration plate, without needing to remove the sealing device. The sealing device, however, may also replaced by other seals before the measurement. With this system, it is possible in particular, but not only, to study substances which are sensitive to air.

Yet a further application of the invention is to remove the sealing device prior to carrying out the desired physical measurements. Removal of the sealing device and subsequent physical measurements may be performed either under an inert gas atmosphere or under air.

If no physical measurements/characterizations are to be carried out in the reaction vessel, then a modified substance or a reaction mixture, or a final product may be removed from vessels, or wells, of a titration plate and optionally studied after processing. All characterizations may be performed manually, semi automatically, or with the aid of fully programmed automated devices.

FIGS. 1, 1a, 2, 3 and 4 illustrate the device according to the invention and the The invention also relates to an arrangement for the chemical or physical modification of substances and their determination by means of spectroscopic methods, consisting of
- a) device consisting of a support (1) and at least two seals (2), which are arranged in a row and are hermetically fitted into cavities (2a), and protrude from the support laterally with respect to inlet and outlet openings, one end of the support being provided with an inlet opening (3) and one end being provided with an outlet opening (4), and the seals being provided with a least one inlet opening (10) and one outlet opening (11), and the support containing at least one first channel (5) which starts at the inlet opening (3) and is continuous, and is arranged in such a way that it opens into the side inlet openings (3a) in the side walls of the seals arranged in a row, and one second channel (6) which starts at the outlet opening (4) and is continuous, and is arranged in such a way that it opens into the side outlet openings (4a) in the side walls of the seals arranged in a row;
- b) a titration plate at least 2 vessels, which are hermetically connected to the seals; and
- c) connections between the inlet and outlet channels to one or more gas sources and/or a vacuum pump.

In a preferred embodiment, the arrangement involves one in which
- b) the vessels are optically transparent or at least transparent for the applied radiation; and additionally
- d) a radiation source for shining light into the vessels; and
- e) a detector for measuring spectral changes are provided.

In particular, the vessels involve titration plates made of an optically transparent material, preferably quartz glass.

The embodiments and preferences described above apply to the individual compo nents of the arrangement. The connections between the inlet and outlet channels may involve hoses or tubes, in which case valves for controlling the gas flow or adjusting the vacuum may be arranged between the gas source or vacuum pump.

Suitable gas sources include protective gases (nitrogen or noble gases), in order to protect substances which are sensitive to air or moisture, or in order to evaporate solvents in a controlled way by passing gases through; reactive gases, for example oxygen, hydrogen, phosgene, carbon monoxide and dioxide, sulphur dioxide; ammonia, amines, phosphine and phosphines, alcohol, aldehydes and ketones, inorganic and organic acids, carboxylic acids and carboxylic acid halides, esters and amides, optionally functionalised olefins (halogenolefins), halogens, hydrogen halides and other chemically reactive gases. Depending on the fluidity of the gases, they may be delivered per se or heated or with inert gases as entrainers.

Suitable radiation sources include lamps (e.g. mercury vapor lamps) or lasers (gas lasers, crystallasers, semiconductor or diode lasers) or sources for X-rays (including synchrotron radiation). Customary optical means for focusing the light beams onto the vessel and a detector may be arranged between the detector and the light source.

Examples of suitable detectors include those for recording spectra in the UV range, visible range and NIR range as well as Raman spectra, and recording powder X-ray diffraction patterns, or spectra resulting from other diffractional methods. All physical measurements may be performed as reflexion or transmission modes.

The arrangement according to the invention is suitable, in particular, for carrying out multiple conversions of various types (high throughput screening, HTS), e.g. for the search for polymorphic forms, formulations, and salts of pharmaceutically active ingredients, or other compounds.

Without being exclusive, such multiple studies relate to the processing of a multitude of chemical experiments which are directed to perform screenings in order to:
- a) Discover and develop polymorphic and pseudopolymorphic forms (hydrates and solvates) of pharmaceutically or agrochemically active ingredients, pigments, dyes, as well as other organic or inorganic compounds, including their amorphous state prepared in the presence of solvents (including water) and solvent mixtures.
- b) Discover and develop of new formulations exhibiting improved properties prepared in presence of solvents or solvent mixtures, excipients, or mixtures of excipients and solvents, or solvent mixtures.
- c) Evaluate suitable crystallisation conditions for the crystallisation of pharmaceutical or agrochemical active ingredients, pigments, dyes, peptides, proteins, as well as other organic or inorganic compounds in presence of solvents or solvent mixtures.
- d) Obtain seed crystals for the preparation of desired crystalline forms of pharmaceutical active ingredients, agrochemical active ingredients, pigments, dyes, peptides, proteins, and other organic or inorganic compounds in presence of solvents (including water) and solvent mixtures.

All conversions may, for example, be suitable: physical conversions of pharmaceuticals, agrochemical active agents, pigments, dyes and other organic or inorganic compounds in the presence of solvents (including water), solvent mixtures, auxiliaries or mixtures of solvents and auxiliaries, in order to produce polymorphic forms, hydrates, solvates, as well as amorphous forms thereof; chemical conversions, for example salt formation, catalytic hydrogenation or oxidation, and study of dyes or dye mixtures. The effect of air and/or particular air humidity, or defined solvent vapors on substances or substance mixtures may also be studied. In aqueous systems said conversions may be induced by variation of the pH-value.

The invention furthermore relates to a method for the simultaneous, physical of chemical modification of substances or substance mixtures in at least two vessels under different physical or chemical conditions, which is characterised in that at least two vessels of the system according the invention are filled with a substance, a sub-stance mixture or a reaction mixture, which are different from one another, and then specific physical conditions are set up or a chemical reaction is carried out.

The embodiments and preferences described above are valid for the method of the invention. In particular, the reaction vessels involve an optically transparent material, preferably in the form of a titration plate, so the products can be measured in the vessel by using spectroscopic methods. The method is more particularly suitable for polymorphism screenings on a multitude of possible chemicals, for a screening of new formulations, as well as for a screening for suitable crystallisation conditions with the use of suitable spectroscopic techniques such as Raman, NIR spectroscopy, optical spectroscopy, and powder X-ray diffraction, or other diffractional methods to characterize the obtained products.

Change in the scope of the invention may, for example, mean the formation of other physical forms (polymorphism), formation of mixed crystals, formation of crystals with different crystal habit, formation of solvates and hydrates, as well as chemical reactions. Such change may be induced through differences of a substance, a sub-stance mixture, or a reaction mixture, for example, the used polymorphic or pseudo-polymorphic form, quantities, quantity ratios, different solvents or solvent mixtures, different excipients (such as pharmaceutical excipients), different reactants or different reaction auxiliaries or quantities thereof (catalysts, co-catalysts). Furthermore, such change may be induced by variable physical conditions, for example pressure, temperature, or flow rate of gases or vapors, irradiation, as well as the duration of processing with the said physical conditions, as well as a combination of the above said parameters.

Change in the scope of the invention may also mean that comparative investigations using stirred or shaken devices, with respect to fixed static devices may be carried out.

The method according to the invention can be carried out in a manner which is known per se. The filling, as well as the spectroscopic measurement of products, can be carried out manually, or automated by using program-assisted control systems. For studies of crystallisation, besides the evaporation of solvents, it is also possible to deliver solvent vapors. Chemical reactions also turn out to be particularly simple since, after the end of the reaction, the used solvents can be fully vaporised and then measurements can be out carried on the reaction residue. In the case of chemical reaction with gases, for example hydrogenations with hydrogen or oxidations with oxygen, the pressure, gas flow and gas quantity can be adjusted accurately.

In a further mode of the invention the investigations may be carried out without using a gas flow after filling of the reaction vessels with all components. If the diameter of the channels is small, then no further measures have to be taken to prevent a mixing of the gaseous components through diffusion. If the channel diameter is larger it may be suitable to seal the inlet and outlet channels.

With multiple studies, a large amount of data on micro scale up to small quantities can be generated in short periods of time by using method according to the invention, so that good economic viability is guaranteed, physical and chemical conditions can be controlled and necessary studies can be significantly accelerated.

As an example, however not being restricted, the method according to the invention is further suitable for the preparation and characterization of crystalline forms, carrying out precipitations being one particular mode.

Furthermore the method of the invention may be employed to screen for suitable crystallization conditions of a multitude of substances, such as pharmaceutically and agrochemically active ingredients, pigments, dyes, peptides, proteins as well as other organic or inorganic compounds in presence of solvents (including water), solvent mixtures, or solvent mixtures with excipients. Particularly in this mode of the performed screening process the addition of suitable seed crystals may be preferred. In yet another application the method of the invention may be applied to screen for suitable seed materials.

As a further example, however not being restricted, the method according to the invention may be employed to obtain in crystalline form, pharmaceutically or agrochemically active ingredients that are by their nature difficult to crystallize. In this mode of the invention crystallizations may be carried out by a slow and controlled addition of a non solvent to a saturated solution of the substance to be crystallized. Generally, the non solvent may be added by directing an inert gas stream which is mixed with a defined vapor pressure of the non solvent through the arrangement of the invention.

Furthermore, the arrangement of the invention may be used to add to an array of saturated, concentrated solutions of a pharmaceutically or agrochemically active ingredient a non solvent in the liquid state. However, here inlet orifices have to be modified such that a defined amount of non solvent may be added to each of the used reaction vessels. This method is particularly suitable for substances which are more easily obtained in the crystalline state, and therefore the non solvent may be added faster.

Furthermore the arrangement of the invention may be employed for the preparation of crystalline salts. For the preparation of crystalline salts, including polymorphs and pseudopolymorphs thereof, solutions of acidic or basic compounds, respectively, are prepared and the reaction vessels are loaded with the prepared solutions. The conversion of the bases or acids, respectively occurs upon addition of a gaseous salt forming compound (such as a hydrogen halide, an inorganic anhydrate, e.g. $SO2$, $SO_3$, organic acids, or basic compound, e.g. ammonia, or amines).

According to the invention crystallizations from supersaturated solutions may be carried out such that the reaction vessels are loaded with solvent and substance while inlet and outlet orifices are closed by a safety valve and through a defined increase of temperature the test substance is fully or partially being dissolved. Subsequently, crystallization is performed by temperature reduction to a desired temperature. An arrangement according to the invention wherein the orifices are closed with a safety valve may also be used to prepare and investigate crystalline substances, crystalline salts or new formulations suspended in various solvents (including water), or solvent mixtures.

In the arrangement according to the invention the nucleation may be induced homogeneously or heterogeneously.

The arrangement according to the invention can be used, for example, in the synthesis of lead structures, the development of synthesis methods, in process development and optimisation, in combinatorial chemistry, in active-agent analysis, active-agent study and active-agent development, food study, environmental analysis and study of catalytic reactions.

The filling of the reaction vessels, the physical measurements (analytical characterisations) of the products, the data/result evaluations may be performed manually, computer aided semiautomatically, or fully programmed automatically.

The following example explains the invention in more detail. As the sealing systems, those as represented in FIG. 1 are used.

EXAMPLE 1

Saturated or unsaturated solutions of carbamazepine are prepared in 43 solvents and solvent mixtures. Inter alia, alcohol, ethers, ketones, hydrocarbons, DMSO, n-methylpyrrolidone and water are used as solvents, and ethanol/water, methanol/water and THE/water in a different mixing ratios are used as solvent mixtures. The intentions of an 8×12 titration plate are respectively filled with 100 of the carbamazepine solutions, so the first six rows of 8 in the plate are filled and could be closed by six sealing systems consisting of a row of 8 seals. A dry nitrogen stream with a flow rate of 0.033 1/min is passed through the first 6 sealing systems. The remaining 6 rows are likewise filled respectively with 100 .d of the carbamazepine solutions and closed by 6 sealing systems of the same geometry. A dry nitrogen stream with a flow rate of 0.43 1/min is passed through these second 6 sealing systems. By means of the two different nitrogen streams, the solvents are evaporated in parallel. After complete evaporation of the solvents, the solids which are formed are studied directly in the wells by means of Raman spectroscopy. The measurements are carried out through the bottom of the titration plate, so that it is possible to work with the exclusion of air humidity. The spectra are assigned to various classes according to their spectral similarity, in which case one class may correspond to one polymorphic or pseudo-polymorphic form.

EXAMPLE 2

2 mg of different hydrates and solvates of carbamazezine are respectively introduced into the wells of a microtitration plate, so that a row of 8 is occupied. This row is closed by a sealing system consisting of a row of 8 seals. A nitrogen stream of 0.5 l/min is passed through this sealing system. After different gas application times, the Raman spectra of the solids are recorded, the gas stream being turned off during the measurement but the wells being closed. These studies make it possible observe the hydrates and solvates.

EXAMPLE 3

Analogous to example 1, the reaction vessels are filled with comparatively less solvent such that suspensions are obtained as starting systems and no gas flow is applied. The investigated substance may be a) dissolved by increasing the temperature and be recrystallised upon subsequent cooling to a defined temperature, or b) the suspensions are kept isothermally for 2 days, or c) the suspensions are exposed to a defined temperature cycle during 2 days, in both cases b) and c) the device is shaken.

The invention claimed is:

1. A device for controlled evaporation of solvents from solutions, comprising:
    a support; and
    at least two seals, which are arranged in a row and are hermetically fitted into cavities of the support, respectively, one end of the support in a longitudinal direction of the support being provided with an inlet opening and another end in the longitudinal direction being provided with an outlet opening, the seals being arranged to protrude from the support orthogonally with respect to the longitudinal direction of the support, and the seals each being provided with at least one cylindrical inlet opening and one cylindrical outlet opening,
    wherein the support includes at least one first channel which starts at the inlet opening of the support and is continuous, and is arranged so as to open into cylindrical side inlet openings of side walls of each of the seals, and wherein the support includes one second channel which starts at the outlet opening of the support and is continuous, and is arranged so as to open into cylindrical side outlet openings in the side walls of each of the seals.

2. The device according to claim 1, wherein the support comprises at least one of metals, glass, quartz, ceramic and reinforced and stiff plastics.

3. The device according to claim 2, wherein the plastics include polytetrafluoroethylene.

4. The device according to claim 1, wherein the support is one-dimensionally designed and contains from 4 to 24 cavities lying in a row.

5. The device according to claim 4, wherein the support corresponds to a length of a side of a macro- or microtitration plate, and to containers arranged in a row thereof, and has cavities corresponding to a number of containers in a row of such titration plate.

6. The device according to claim 1, wherein the support has a thickness of from 4 mm to 4 cm.

7. The device according to claim 1, wherein the cavities are cylindrical.

8. The device according to claim 7, wherein a diameter of the cavities is from 2 mm to 5 cm.

9. The device according to claim 1, wherein a diameter of the channels is from 10 µm to 10 mm.

10. The device according to claim 1, wherein mutually opposite openings of the at least one inlet channel and of the outlet channel at the ends of the support are provided with hermetically fitted glands in the form of short tubes.

11. The device according to claim 1, wherein the seals have a flat surface at a protruding end.

12. The device according to claim 1, wherein a circumferential sealing lip is fitted above the flat surface.

13. The device according to claim 1, wherein each seal comprises a thermoplastic or elastomeric plastic.

14. The device according to claim 1, wherein the at least one cylindrical inlet opening and the at least one cylindrical outlet opening are arranged at opposite edges of the seal at an end of a protruding part of the seal.

15. A system for controlled evaporation of solvents from solutions in at least two vessels, comprising:
    a device according to claim 1; and
    at least two vessels which are hermetically connected to the seals.

16. The system according to claim 15, wherein the vessels are provided as individual vessels or as vessels connected as a one-dimensional or two-dimensional row or arrangement.

17. The system according to claim 15, wherein the vessels include a plate with wells at an equal spacing, in a one- or two-dimensional row arrangement and cylindrical wells with a flat or rounded bottom.

18. The system according to claim 17, wherein a volume of the wells is from 10 µl to 5 ml and a diameter of the wells is from 10 µm to 3 cm.

19. The system according to claim 17, wherein the plate comprises a standardized macro- or microtitration plate with a defined number of wells.

20. The system according to claim 15, wherein the device includes 2 to 24 seals, the system further comprising:
    a titration plate made of an optically transparent material, the titration plate having wells to which the seals of the device are hermetically connected.

21. The system according to claim 20, wherein the titration plate comprises quartz.

22. The system according to claim 20, wherein the device comprises a one-rowed arrangement of seals, which are hermetically connected to a row of wells in the titration plate.

23. The system according to claim 20, wherein the device comprises a one-rowed arrangement of seals, and from at least two to all rows of wells in the titration plate are hermetically connected to a one-rowed arrangement of seals.

24. The system according to claim 20, wherein the device includes 4 to 16 seals.

25. A method for the controlled evaporation of solvents from solutions in at least two vessels under different physical or chemical conditions, wherein the at least two vessels of the system according to claim 15 are filled with a substance, a substance mixture or a reaction mixture, which are different from one another, and then specific physical conditions are set up.

26. The method according to claim 25, wherein the system includes an arrangement for the controlled evaporation of solvents from solutions in vessels of a titration plate and their determination by means of spectroscopic methods, comprising
    the device;
    a titration plate comprising the at least two vessels, which are hermetically connected to the seals of the device; and connections between the inlet and outlet channels to one or more gas sources and/or a vacuum pump.

27. The method according to claim 25, wherein the system includes an arrangement for the controlled evaporation of solvents from solutions in vessels of a titration plate and their determination by means of spectroscopic methods, comprising the device;

a titration plate comprising the at least two vessels, which are hermetically connected to the seals of the device, wherein the vessels are optically transparent;

connections between the inlet and outlet channels to one or more gas sources and/or a vacuum pump;

a radiation source for shining light into the vessels; and a detector for measuring spectral changes, wherein changes of substances or substance mixtures are measured by means of spectral changes or powder X-ray diffraction.

28. An arrangement for controlled evaporation of solvents from solutions in vessels of a titration plate and their determination by means of spectroscopic methods, comprising:

a device including a support and at least two seals, which are arranged in a row and are hermetically fitted into cavities of the support, respectively, one end of the support in a longitudinal direction of the support being provided with an inlet opening and another end in the longitudinal direction being provided with an outlet opening, the seals being arranged to protrude from the support orthogonally with respect to the longitudinal direction of the support, and the seals each being provided with at least one cylindrical inlet opening and one cylindrical outlet opening, wherein the support includes at least one first channel which starts at the inlet opening of the support and is continuous, and is arranged so as to open into cylindrical side inlet openings of side walls of each of the seals, and wherein the support includes one second channel which starts at the outlet opening of the support and is continuous, and is arranged so as to open into cylindrical side outlet openings in the side walls of each of the seals;

a titration plate comprising at least two vessels, which are hermetically connected to the seals; and connections between the inlet and outlet channels to one or more gas sources and/or a vacuum pump.

29. The arrangement according to claim 28, wherein the vessels are optically transparent, and wherein the arrangement further comprises:

a radiation source for shining light into the vessels; and a detector for measuring spectral changes.

* * * * *